(12) United States Patent
Rice et al.

(10) Patent No.: US 11,510,724 B2
(45) Date of Patent: Nov. 29, 2022

(54) OPERATING ROOM MULTIFUNCTION CABLE SYSTEM

(71) Applicants: Jonathan Rice, Camarillo, CA (US); Erik C. Spayde, Westlake Village, CA (US)

(72) Inventors: Jonathan Rice, Camarillo, CA (US); Erik C. Spayde, Westlake Village, CA (US)

( * ) Notice: Subject to any disclaimer, the term of this patent is extended or adjusted under 35 U.S.C. 154(b) by 0 days.

(21) Appl. No.: 16/877,271

(22) Filed: May 18, 2020

(65) Prior Publication Data

US 2021/0038285 A1 Feb. 11, 2021

Related U.S. Application Data

(63) Continuation of application No. 15/242,195, filed on Aug. 19, 2016, now Pat. No. 10,653,473.

(51) Int. Cl.
*A61B 18/00* (2006.01)
*A61B 18/14* (2006.01)

(52) U.S. Cl.
CPC .... *A61B 18/14* (2013.01); *A61B 2018/00166* (2013.01); *A61B 2018/00178* (2013.01); *A61B 2018/00595* (2013.01); *A61B 2018/1475* (2013.01); *A61B 2218/008* (2013.01)

(58) Field of Classification Search
CPC .......... A61B 2018/00166; A61B 2018/00178; A61B 2018/00595; A61B 2018/1475; A61B 2218/008
See application file for complete search history.

(56) References Cited

U.S. PATENT DOCUMENTS

| 5,275,596 | A | * | 1/1994 | Long | A61B 18/14 606/28 |
| 6,716,233 | B1 | * | 4/2004 | Whitman | A61B 17/07207 606/219 |
| 8,303,581 | B2 | * | 11/2012 | Arts | A61B 18/24 606/41 |
| 2002/0019631 | A1 | * | 2/2002 | Kidder | A61B 18/1402 606/42 |
| 2006/0258955 | A1 | | 11/2006 | Hoffman et al. | |
| 2007/0179498 | A1 | * | 8/2007 | MacDonald | A61B 18/1485 606/45 |
| 2008/0200940 | A1 | | 8/2008 | Eichmann et al. | |
| 2009/0247829 | A1 | | 10/2009 | Adachi et al. | |
| 2009/0312752 | A1 | * | 12/2009 | Djordjevich | A61B 18/20 606/10 |
| 2012/0226273 | A1 | | 9/2012 | Nguyen et al. | |
| 2012/0283728 | A1 | * | 11/2012 | Cosmescu | A61B 18/1477 606/45 |
| 2014/0163595 | A1 | | 6/2014 | Witt et al. | |

* cited by examiner

*Primary Examiner* — Pete T Lee
(74) *Attorney, Agent, or Firm* — Stefan J. Kirchanski; Matthew J. Spark; Zuber Lawler LLP (57) ABSTRACT

An improved multifunction cable for use in an operating room avoids the usual tangle of wires and tubes can be a significant hazard. The cable comes pre-sterilized with a number of wires and tubes pre-installed in a protective housing making it easy to conduct myriad wires and tubes from one region of the operating room to another without any possibility of tangling or violation of sterility. At the sterile end of the cable a special terminus acts as a holder to keep the various operating instrument organized. The terminus is designed to accept a special smoke evacuating monopolar electrosurgery instrument.

8 Claims, 5 Drawing Sheets

OPERATING ROOM MULTIFUNCTION CABLE SYSTEM

CROSS-REFERENCE TO PRIOR APPLICATIONS

This application is a continuation of U.S. patent application Ser. No. 15/242,195, filed Aug. 19, 2016, which issued as U.S. Pat. No. 10,653,473 on May 19, 2020.

U.S. GOVERNMENT SUPPORT

Not applicable

BACKGROUND OF THE INVENTION

Area of the Art

The present invention is in the art of health care and is directed to an improved cabling system for use with commonly used surgical tools that improves the surgeon's experience, diminishes setup time, and improves sterility over the current standard.

DESCRIPTION OF THE BACKGROUND

For much of human history the role of microorganisms in infection was unknown. It was expected that wounds either from accident or medical procedures would become inflamed and pus-filled. This was thought to be a natural part of healing. Now, of course, we know better and great efforts are made to ensure sterility during medical procedures. However, the ever increasing news about "super bugs" and fatal infections acquired in hospitals is resulting in increased awareness and the relevance of discovering ways to more effectively combat infections.

There appear to be several factors at play here. First, the widespread availability of antibiotics following the end of World War II has resulted in medical protocols becoming somewhat lax. Prior to the advent of antibiotics, a hospital acquired infection, particularly a surgical site infection (SSI) was serious and often fatal. As a result, great pains were taken to keep all parts of the hospital as sterile as possible. However, antibiotics were able to cure most infections so medical personnel became less and less careful. Why spend a great deal of money avoiding an infection that could easily and cheaply be cured? At the same time life-saving antibiotics became increasingly used in industrial animal husbandry to reduce cost and accelerate growth of animals raised for human consumption. Antibiotics were and are used in vast quantities to treat animal infections and generally shortcut the need for cleanliness and conditions that spread infection in industrial farms. The use of antibiotics in food production was highly profitable and seemed harmless.

However, industrial use of drugs designed to save human lives turns out to be incredibly harmful. Chronic use of antibiotics in animal husbandry causes the rapid evolution of drug-resistant "super bugs." Many communities have become infected with drug resistant microorganisms from their drinking water. Furthermore, the meat from treated animals often contains drug resistant microorganisms because such agents are released during slaughter and contaminate the meat.

The growing prevalence of antibiotic resistance makes healthcare-associated infection increasingly serious. While some improvement has been noted, these infections remain a significant problem. The CDC Procedure Associated Module "Surgical Site Infection (SSI) Event Introduction" (January 2016 edition) states:

In 2010, an estimated 16 million operative procedures were performed in acute care hospitals in the United States. A recent prevalence study found that SSIs were the most common healthcare-associated infection, accounting for 31% of all HAIs among hospitalized patients. The CDC healthcare-associated infection (HAI) prevalence survey found that there were an estimated 157,500 surgical site infections associated with inpatient surgeries in 2011. NHSN data included 16,147 SSIs following 849,659 operative procedures in all groups reported, for an overall SSI rate of 1.9% between 2006-2008. A 19% decrease in SSI related to 10 select procedures was reported between 2008 and 2013. While advances have been made in infection control practices, including improved operating room ventilation, sterilization methods, barriers, surgical technique, and availability of antimicrobial prophylaxis, SSIs remain a substantial cause of morbidity, prolonged hospitalization, and death. SSI is associated with a mortality rate of 3%, and 75% of SSI-associated deaths are directly attributable to the SSI.

The modern operating room (OR) presents multiple dangers of infection. For many years the procedure has been to sterilize the OR as well as possible prior to use. The patient's skin is surface sterilized, and then the patient is draped with a sterile covering so that only the site of the actual operation is exposed. Instruments are sterilized and even the air is filtered to reduce or eliminate airborne contaminants. Personnel who directly approach the patient wear sterile garments and scrub prior to the operation. However, while instruments that directly contact the patient can be sterilized, a tremendous number of medical instruments (particularly electronic devices) cannot be sterilized in the usual way. Of course, the surfaces of diagnostic devices and power supplies for instruments (e.g., electrocautery devices) can be wiped with disinfectants. However, OR sterility is further ensured by placing all such inherently non-sterile devices away from the sterile field of the OR. The wires and tubes leading from the instruments are led over or through the drape and the ends approaching the patient are sterile. Yet as more and more complex systems are introduced, there is an increasing danger that a non-sterile tube or wire will slip or fall into the sterile region of the OR and compromise sterility. And any compromise of sterility carries the danger of an infection that may prove very difficult and very expensive to treat.

SUMMARY OF THE INVENTION

The present invention includes an improved multi-function cable for use in an operating room. Traditionally, the wires and tubes needed to power each surgical instrument are individually threaded from a non-sterile to a sterile region in the operating room. This veritable tangle of wires and tubes can be a significant hazard. The tangle makes it much easier to inadvertently drop or pull a sterile instrument into the non-sterile region. If medical personnel become entangled, even greater problems may ensue. Furthermore, the setup involved with the current standard of passing each individual tube or wire (such as for the monopolar electrosurgery device, bipolar electrosurgery, suction tubing, smoke evacuator, or other specialized tools) from the sterile field to the circulating nurse to attach to the non-sterile source end is tedious, time-consuming and archaic.

The multifunction cable comes pre-sterilized and encases a number of wires and tubes in a protective housing making it possible to replace routing a myriad wires and tubes from one region of the operating room to another with the positioning of a single cable thus avoiding any possibility of tangling. The unitary cable can be readily fastened to sterile drapes and to the operating table. At the non-sterile end of the cable ordinary, individual wires and tubes fan out for connection to various power sources and machines. At the sterile end of the cable a special terminus acts as a holder to keep the various operating instrument organized. Mechanisms within the terminus allow the instruments to be individually pulled away from the terminus with the terminus unwinding additional tubing or wire as needed. When an instrument is no longer needed, a simple button push retracts the instruments into the terminus.

This retraction anti-tangle feature makes the terminus particularly useful with a unitary smoke evacuating monopolar electrosurgery instrument. The instrument has smoke evacuation opening near its operating tip. The electrical lead and suction tube from the terminus attach to the proximal end of the monopolar instrument and are either coaxial or joined side by side to avoid tangles and avoid altering the "feel" and mobility of the monopolar.

DESCRIPTION OF THE FIGURES

FIG. 3 is a diagrammatic view emphasizing the sterile and non-sterile areas of an operating room employing the inventive cable; area FIG. 3A outside the broken lines showing the non-sterile area of an operating room employing the inventive cable; area FIG. 3B within the broken lines showing the sterile area of an operating room employing the inventive cable.

FIG. 4 shows the tools in use.

DETAILED DESCRIPTION OF THE INVENTION

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide an improved OR cabling system to help ensure OR sterility while diminishing setup time significantly and improving the surgeon experience by allowing ease of use, elimination of tangling of wires/tubes and seamless transitioning between use of different equipment.

With more than an estimated 234 million major surgical operations occurring worldwide every year according to the WHO (Lancet, 2008), there is a continual need to improve various aspects of surgery, whether it be to provide advantages to surgeons and assistive personnel, diminish cost, improve efficiency and/or minimize OR time. While there are variable surgical sterile and equipment setups depending on the type of surgery and surgeon preference, there are some basic drape and equipment setups that are common for the vast majority of major surgical procedures. Most major operations begin with the anesthetization of a patient followed by the positioning of the patient, which is then followed by the sterile preparation of the surgical area with surgical draping and setup of surgical equipment prior to the incision or surgical approach being initiated. The most common practice implemented presently for surgical setup is the use of disposable draping with the passing of wires or tubes of surgical devices that require connection to a power source, typically located outside of the sterile field. This includes the commonly used electrocautery/electrosurgery devices (including monopolar devices known a "bovie" or "Bovie" which is a registered trademark of Bovie Medical Corporation of Clearwater, Fla., bipolar forceps), suction tubing, various other fluidics and often a powered drill or saw. There can be other devices, such as light cables or other specific surgical apparatuses that may be also utilized during surgery; however uniformly, the electrocautery and suction devices with associated wiring/tubing represent the most commonly used equipment utilized across numerous surgical practices.

The current invention is a simple, yet useful improvement involving the draping and surgical tools with non-sterile source attachments that are cost effective, diminish the setup time for surgical preparation, as well as be more efficient for surgeons/assistive personnel in addition to improving sterile procedure and diminishing surgical infection rates. Few new products offer such pan-improvement potential. The mechanics involved in the setup for commonly used surgical devices described above (monopolar instrument, bipolar forceps, and suction tubing) typically entails draping the patient sterilely and then setting up the monopolar electrosurgery device, bipolar forceps, suction tubing and drill/saw by a sterile, gowned individual who passes the source ends of the wires/tubing to an OR nurse or other non-sterile personnel, who then attach the now-contaminated end of the tubing/wiring to non-sterile power sources. The tubing and wiring are then generally secured at a certain point on the drape to allow for sufficient slack of the sterile end of the tubes and wires for the surgeon to operate and also to prevent the non-sterile portion of the tubing from sliding back onto the sterile field, which would result in contamination of the sterile field.

There are a number of problems associated with this system of individually handing off numerous wires/tubes. First, each of the common non-sterile source requiring apparatuses have to be uncoiled, passed to the nurse, connected to the non-sterile source, then secured to the drape, often by poorly-designed (often hook and loop fastener) straps that are built-in features for most disposable surgical drapes. This process of individually passing each wire, preparing the wires/tubes from their coiled/bound initial state requires considerable time—minutes when considering the separate steps involved with each entity. A second issue with the current protocol is sterility. The more separate wires that exist, the greater the opportunity there is for a wire or tubing to slip from the point of drape attachment, or to adhere to one of the other wires or tubes present and violate sterility. Wires and tubes will often become tangled because a surgeon will often alternate between usage of different surgical tools with the ensuing tangling of tubing/wiring increasing the risk of surgical tools for falling off the table or dropping low enough on the table to compromise sterility. A third issue is the cost of the various disposables. Each separate wire or tube can cost a significant amount of money. The cost of an infection, plausibly contributed to or caused by contamination from migration of wire/tubing migration from non-sterile field to sterile field, can cost astronomically more.

Rather than have separate cables for the above mentioned devices, a specialized, multi-purpose cable is provided, which includes separate internalized conduits for bipolar forceps, monopolar electrocautery/electrosurgery, suction tubing and other apparatus such as fluidics bipolar electrocautery with alternate embodiments of the inventive cable incorporating additional wiring for drill and powered saw function.

The cable arrives preassembled and pre-sterilized. The cable is a more or less solid unit with separate conduits for the various components within the main cable. One possible manufacturing approach is a flexible plastic foam core having cavities for the various conduits and wrapping sheath or outer cover to provide stability. Such a foam core can be produced with molded cavities and the components can be threaded through during the manufacturing process with the outer sheath being coated or wrapped around the core, or the components can be threaded through the sheath and the foam then injected. Alternatively, the outer cover can enclose a hollow space (rather like the lumen of a pipe) through which the various components are threaded during the manufacturing process. The advantage of the foam core is that it prevents accidental short circuits, etc. The sheath cable is insulated to withstand moisture and heat and strong enough to resist crushing, thus protecting the internal components. It is envisioned that the cable would be assembled from sterile components under clean room conditions. However, following assembly the cable would receive an additional sterilization. The cable comes preassembled (with different packages for different types of specialties/surgeries). The cable has in its elemental state, wiring/tubing that is identical or similar to existing wires/plugs, etc. so as to be functional by attaching or plugging into the currently used power sources.

The main cable can have individualized branches that separate out on both the sterile terminus where instruments are attached in the OR and on the non-sterile source end of the cable where individual connection fan out to allow various tubes and wires to attach to power sources (e.g., monopolar, bipolar, suction, additional component such as drill, neuromonitoring sources, etc.). This fanning out allows ease of connection to the power sources. Likewise, on the sterile, surgeon end of the cable, there can be separation of wires/tubing to enable use of any of the components without interference by proximity of the other surgical instruments, while maintaining short enough lengths of the tubing/wiring on the surgeon/sterile portions distal to the separation of the cable into the individual wires/tubes to minimize the risk of any of the components falling off the side of the table and becoming contaminated. The cable can also feature a state of the art, non-fail securing mechanism to maintain the cable in a fixed position on the surgical drape. For example, rather than relying on hook and loop fasteners, both the cable and the drapes can be equipped with integral rings (D-rings in the case of the drapes and molded in loops in the case of the cable) and a simple, yet reliable mechanical linkage such as a carabineer is employed to link the rings. This mechanism further minimizes the risk of any part of the sterile side of the cable falling off of the table or to non-sterile levels as well as prevent the dragging of non-sterile tubing back onto the surgical field as can frequently happen with prior art components.

The multifunction surgical cable will yield advantages over the primitive, existing OR standard by providing a product that:
  is easier, faster, simpler to set up than the current devices, being more cost effective than the cumulative cost of all the individual devices' tubing/wiring;
  diminishes the risk of contamination of sterile field, thereby less likely to cause infection than the current, outdated practice;
  reduces time spent setting up and disposing of multiple wiring/tube components;
  significantly diminishes the tangling of wiring/tubing of surgical devices, thus improving the surgeon's experience;
  reduces the incidence of surgical delays for untangling of wires/tubing or replacement of tools that have become contaminated;
  reduces cost by diminishing/eliminating contamination, replacement of contaminated instruments; and
  facilitates use of a new monopolar electrosurgery device which has suction built into the housing to provide for efficient, internalized smoke evacuation.

Figure 1:
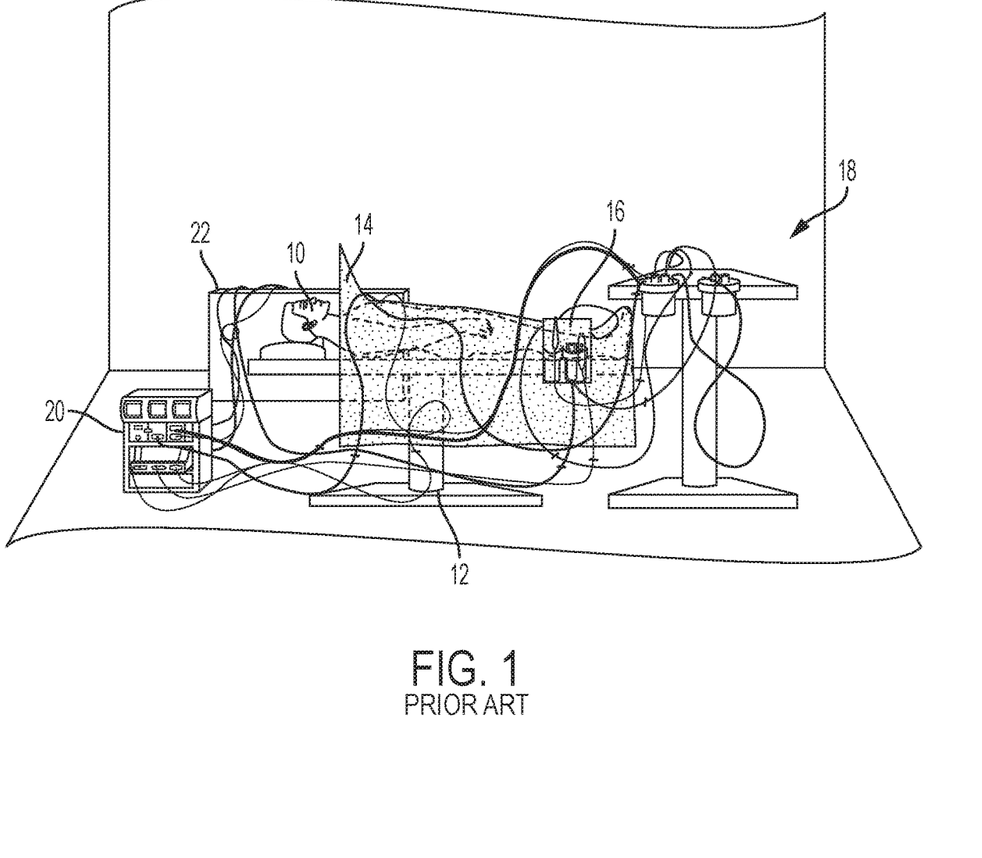
FIG. 1 shows a diagrammatic view of a PRIOR ART operating room.

FIG. 1 shows the general layout of a PRIOR ART operating room. A patient 10 is disposed on an operating table 12 and covered with a sterile drape 14. A package of operating instruments 16 is attached to the drape 16. A veritable tangle of connecting conduits and wires connects the instruments 16 with various power sources such as suction devices 18 and bipolar cautery power supply 20. For sake of illustration, several of the power sources are shown as being very close to the patient. In actual operating rooms, these non-sterile devices may be located at a distance behind a sterile drape or barrier 21.

Figure 2:
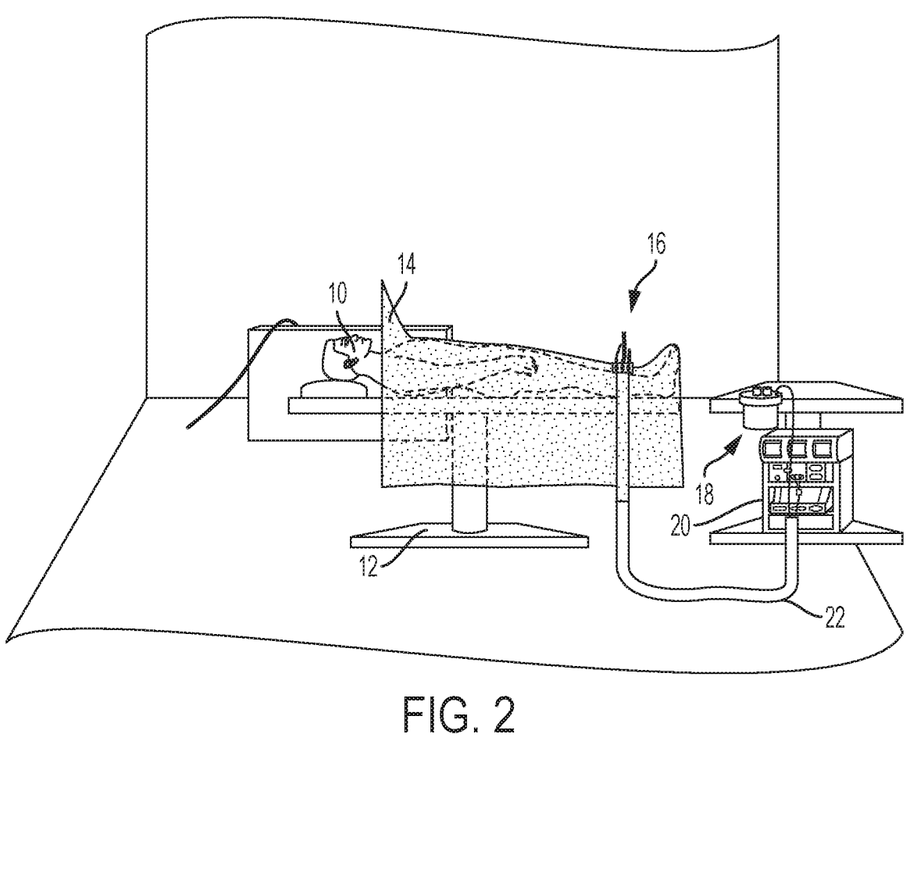
FIG. 2 is shows a diagrammatic view of an operating room with the inventive cable.
Figure 3A:
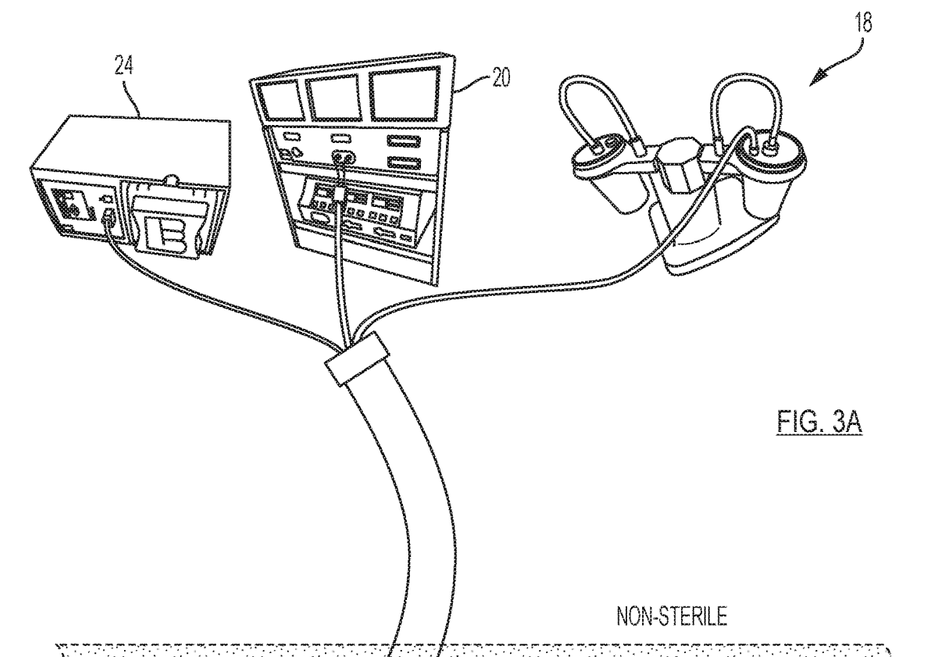
Figure 3B:
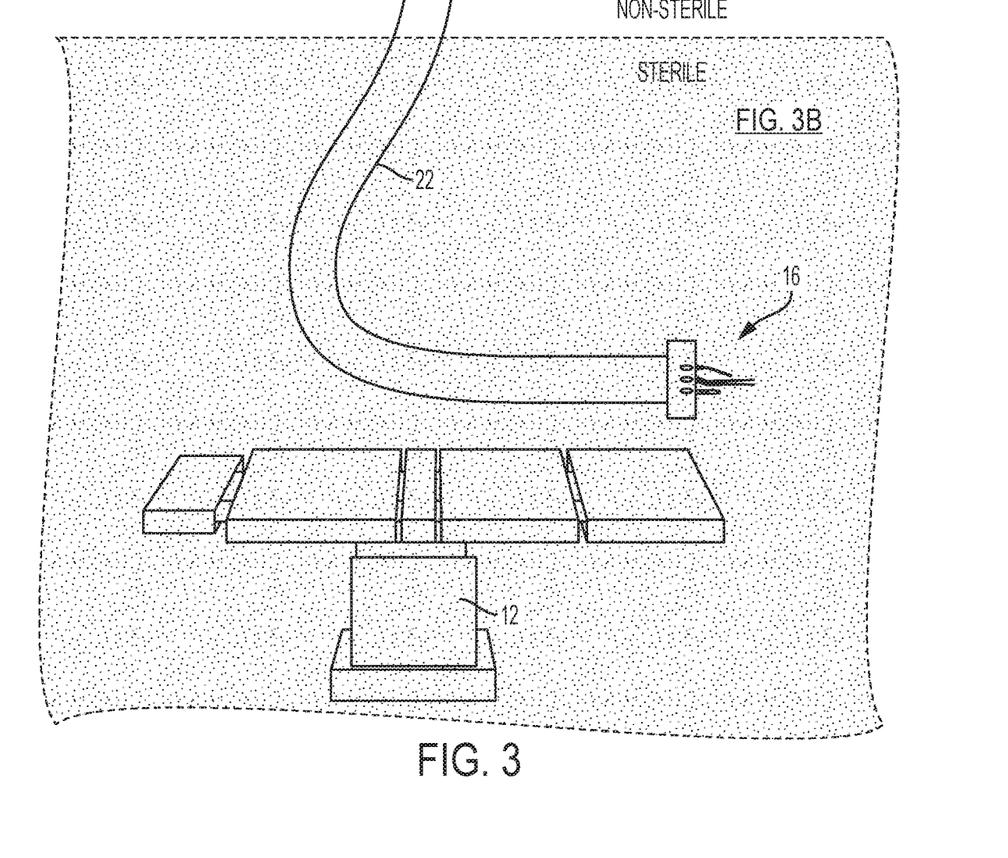

FIG. 1 should be contrasted with FIG. 2 which shows the multifunction cable 22 in the OR. It stretches from the non-sterile portion of the suite to the sterile table 12 itself. FIG. 3 is a diagrammatic layout to emphasize the sterile A versus non-sterile B regions of the room. The cable 22 stretches from one region to the other. In the non-sterile region power sources for various instruments such as suction 18, bipolar electrocautery 20 and monopolar electrocautery/electrosurgery. The A and B regions are shown in a single plane for simplicity of illustration. As previously explained, the sterile and non-sterile regions are separated by horizontal distance along the same floor with barriers such as sterile drapes separating the regions. The cable 22 is threaded over the sterile drape and attached thereto. Generally, the entire floor is considered to belong to the non-sterile region. For simplicity of illustration the cable 22 is not drawn to scale. While the precise diameter of the cable 22 will vary depending how many wires/conduits are enclosed, the typical diameter would between 1 and 2 inches (about 2.5-5 cm).

The multifunction cable 22 is available in several configurations to mate with common OR equipment. Adaptor modules are also available to connect to less common equipment. The cable unit 22 comes pre-sterilized in a sterile and easy to open package. While it might be possible to resterilize the unit for reuse, this is strongly discouraged because of the danger of infectious organisms lodged within the suction ports of the device. For use, the cable is removed from its sterile package and laid out in the OR. Next, the surgeon or other personnel attaches the desired instruments to the terminus 26 of the cable.

Figure 4A:
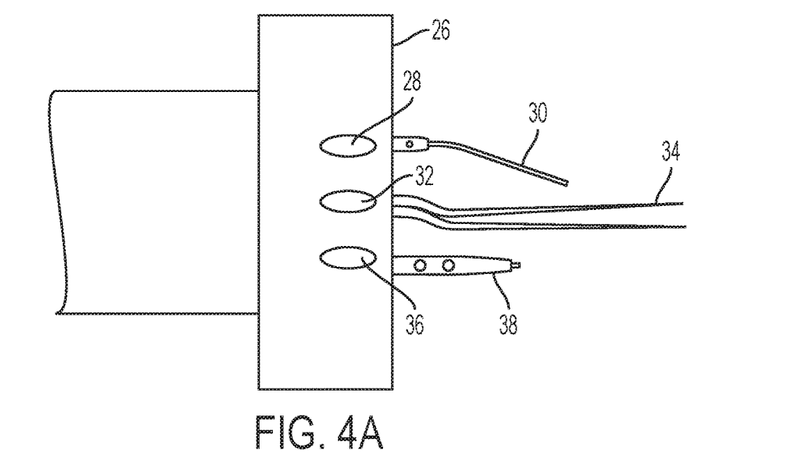
FIG. 4A shows the tools all retracted.
Figure 4B:
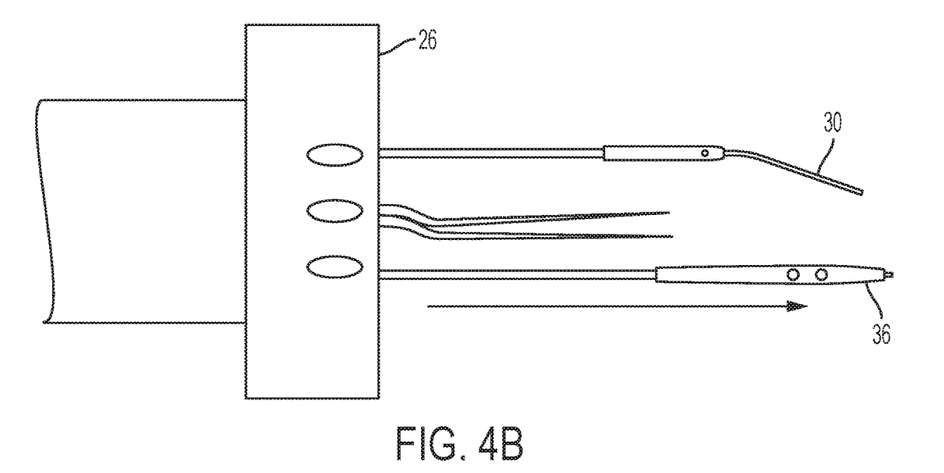
FIG. 4B shows two tool in an extended position.
Figure 4C:
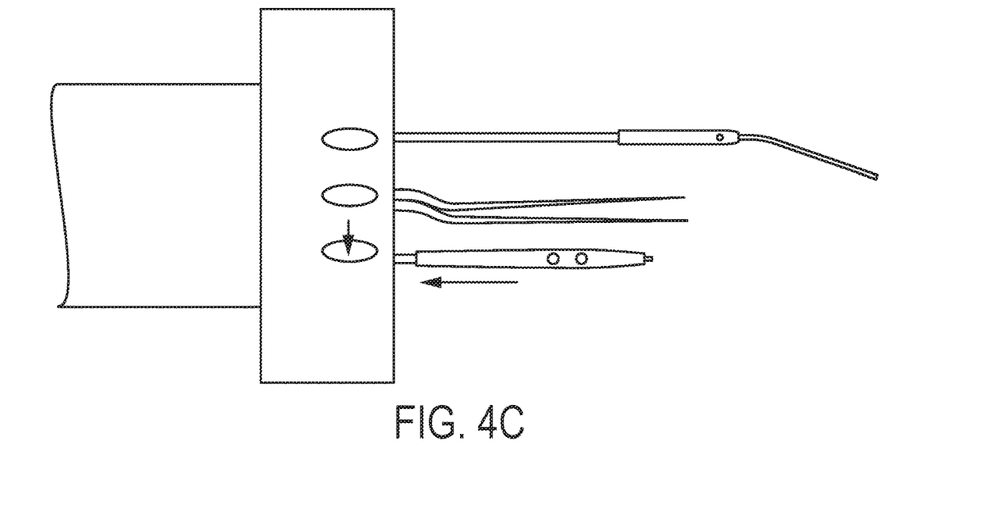
FIG. 4C shows one of the extended tools of FIG. 4B being retracted.

The terminus 26 is somewhat larger than the rest of the cable 22 and can be firmly attached to the drape or table as desired (in place of the package 16 shown in FIG. 2). The terminus 26 contains connections (electrical, suction and/or other fluidic sources) for the attached instruments. The terminus 26 also contains a plurality of "hose reel" mechanisms, one for each attachable instrument. The reel is a spring loaded spool around which is wound a length of tubing or wire (depending on the instrument) that connects at its distal end with the instrument and at its proximal end with the proper channel within the multifunction cable 22. FIG. 4A shows the terminus 26 which has a button associated with each instrument (button 28 for suction probe 30; button 32 for bipolar forceps 34; and button 36 for monopolar electrosurgery instrument 38). As shown in FIG. 4B, the surgeon merely pulls out an adequate length of wire or tubing for use of a given instrument during the procedure. Additional tugging will advantageously release additional wire or tubing. As shown in FIG. 4C, the surgeon, at any time, can touch the appropriate button on the terminus 26 to retract the instrument to the home position or to shorten the lead appropriately. In this way tangles are avoided.

Figure 5:
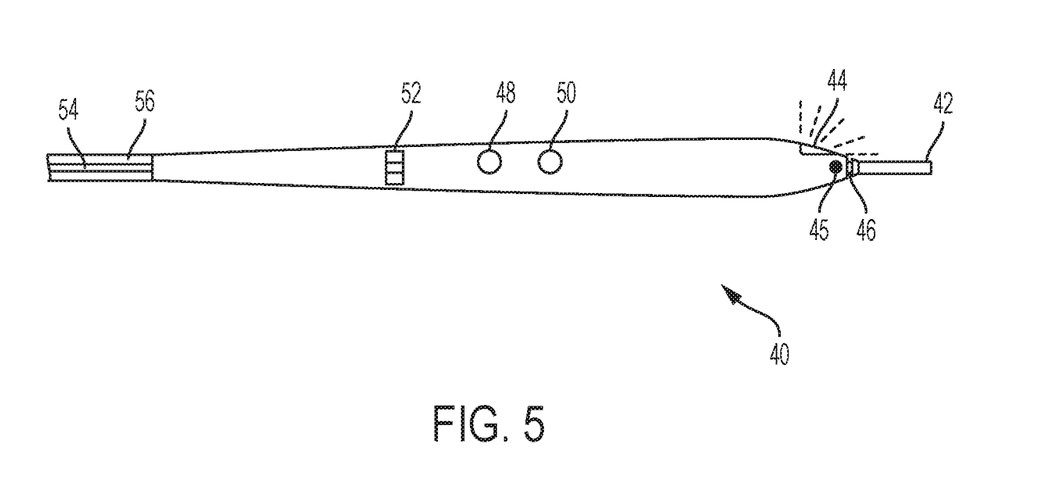
FIG. 5 show an inventive monopolar electrocautery device that is particularly adapted to use with the present invention.

The cable 22 and instrument station terminus 22 is ideally suited to use with a new design monopolar electrosurgery instrument 40 (FIG. 5). The prior art monopolar electrosurgery instrument 38 consists of a single electrical wire attaching to non-sterile power source with plastic housing which contains two buttons, one for 'coagulation' function and the other for 'cutting' function. Both functions are a form of electrocautery. Cauterizing tissue results in the production of fumes and smoke, not unlike the production of smoke/fumes resulting from grilling beef. These fumes are hazardous to anyone inhaling them. Significantly, the fumes also often obstruct the surgeon's vision. Moreover, studies have shown the fumes to have carcinogenic potential. As a result various smoke evacuation systems have been developed to address this problem. However, these systems consist of awkward, secondary systems in which a separate suction tubing is utilized with bulky, awkward secondary attachment mechanisms which attach to the monopolar instrument. Although many of these systems may be adequate for capturing and removing the majority of the fumes from electrocautery, they hinder the use of the instrument by changing its feel and dynamics. Having two leads attached to the device enhances the likelihood of tangles and hang-ups. Often, the surgeon is forced to remove the smoke evacuation apparatus if the region when electrocautery is called for is in a tight space, as often occurs in deep wounds.

An advantage of the inventive monopolar instrument 40 is that the smoke evacuation feature is built-in and does not significantly change the dimensions or tactile feel of the instrument. Similar to the "classic" instrument 38, the improved instrument 40 has two control buttons 48, 50 which control coagulation and cutting. In addition, the instrument has a slide control 52 for a built-in light 44 which is located at the distal end of the instrument near the metallic cutting tip 42. Also near the tip 42 is a circumferential groove 46 for smoke evacuation thereby resulting in nearly immediate suctioning of the fumes from their point of creation (the tip 42). It will be understood that openings within the groove are in fluidic communication with the suction tubing at the proximal end of the instrument. Of course, the groove 46 could be replaced by holes or screened opening near the tip, but the current design is particularly effective at drawing smoke away from the tip 42 (because of the proximity of the groove 46) while the design resists clogging because the actual openings to the suction system are recessed within the groove. The introduction of a light 44 to illuminate the metallic tip 42 is a beneficial feature when electrocautery is being performed in a region where overhead lighting may not be adequate, such as when operating in tight quarters of a wound where overhead lighting may be obscured by more superficial tissue. The light 44 is controlled by the switch 52 which can be set in either an "on" or "off" mode. In addition, the switch can set an "automatic" mode where the light is activated automatically when either one of the power buttons 48, 50 is pressed or when illumination reaching the tip 42 falls below a preset value (as detected by a photocell 45). In this mode, the light automatically activates without the surgeon having to take any action if the tip 42 is placed in a shadowed region.

The improved monopolar instrument 40 works ideally with the retraction feature of the terminus 26. The instrument 40 has both a suction lead 56 and an electrical lead 54. The two leads can be side-by-side or coaxial. The proper connections to suction and electrical conductors is made in the terminus 26 so only a relatively short distance of coaxial or side-by-side leads are exposed. In either configuration the leads are handled by a retractor system like the original monopolar instrument 38, thus avoiding the complexity and possibility of tangles when this instrument 40 is connected "classically" to separate electrical and suction sources.

All or most of the cable 22 and its associated parts are intended to be disposed of after the procedure. Most of the wires and conduits currently in use are disposable. Most of the operating instruments (but not the power sources) are similarly disposable although some parts, such as the monopolar electrosurgery tips, may be recycled. Although the terminus 26 and the cable 22 could be supplied separately making it possible to "mix and match" to create a variety of different set ups, supplying the cable 22 and the terminus 26 as a preassembled unit ensures ease of set up and minimizes contamination problems. One goal of the invention is for the proposed cable to be a seamless transition for surgeons and existing OR equipment. Just as the current setup for monopolar electrosurgery devices, bipolar forceps and suction instruments involves passing off the wires to non-sterile personnel to attach to non-sterile sources, and selection and connection of sterile instruments of surgeon's choice to the sterile ends of the respective wires/tubes, the OR cable's separate conduits fanning out from the nonsterile end of the cable to plug into the non-sterile sources in the same manner as the individuals current standard wires and tubes do. Likewise, the surgeon can plug in whatever bipolar forceps he/she chooses into the designated bipolar tubing connection port at the terminus. The same applies for the connection of the suction apparatus (e.g., Frasier tip, Yankauer tip). The major variation from the current standard is that the inventive cable 22 would come out of the box with the novel, internalized smoke evacuation monopolar design 40.

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

What is claimed is:

1. A monopolar electrosurgery/electrocautery instrument comprising:
    an elongate housing;
    a tip disposed at a first end of said housing;
    a light disposed near the tip;
    a photocell for automatically controlling the light;
    a smoke evacuator disposed in proximity to the tip; and
    a length of suction tubing and a length of electrical lead disposed at a second end of said housing wherein the suction tubing is in fluidic communication with the smoke evacuator.

2. The monopolar electrosurgery/electrocautery instrument according to claim 1 further comprising a manually operated switch for the light.

3. The monopolar electrosurgery/electrocautery instrument according to claim 1, wherein the length of suction tubing and the length of electrical lead are coaxial.

4. The monopolar electrosurgery/electrocautery instrument according to claim 1, wherein the smoke evacuator comprises a circumferential groove.

5. A monopolar electrosurgery/electrocautery instrument comprising:
    an elongate housing;
    a monopolar electrosurgery metallic tip disposed at a first end of said housing;
    a light disposed near the tip;
    a photocell for automatically controlling the light;
    a smoke evacuator disposed in proximity to the tip; and
    a length of suction tubing and a length of electrical lead disposed at a second end of said housing wherein the suction tubing is in fluidic communication with the smoke evacuator.

6. The monopolar electrosurgery/electrocautery instrument according to claim 5 further comprising a manually operated switch for the light.

7. The monopolar electrosurgery/electrocautery instrument according to claim 5, wherein the length of suction tubing and the length of electrical lead are coaxial.

8. The monopolar electrosurgery/electrocautery instrument according to claim 5, wherein the smoke evacuator comprises a circumferential groove.

* * * * *